| United States Patent [19] | [11] | 4,184,921 |
|---|---|---|
| Roeschlau et al. | [45] | Jan. 22, 1980 |

[54] PROCESS AND REAGENT FOR DETERMINING CHOLESTEROL

[75] Inventors: Peter Roeschlau, Seeshaupt; Erich Bernt, München; Wolfgang Gruber, Tutzing-Unterzeismering, all of Fed. Rep. of Germany

[73] Assignee: Boehringer Mannheim GmbH, Mannheim-Waldhof, Fed. Rep. of Germany

[21] Appl. No.: 900,958

[22] Filed: Apr. 28, 1978

Related U.S. Application Data

[63] Continuation of Ser. No. 695,332, Jun. 14, 1976, abandoned.

[30] Foreign Application Priority Data

Mar. 25, 1976 [DE] Fed. Rep. of Germany ....... 2612725

[51] Int. Cl.$^2$ ............................................. G01N 31/14
[52] U.S. Cl. .................................................... 435/11
[58] Field of Search .............. 195/103.5 R, 99, 100; 23/230 B, 230 R; 252/408 R

[56] References Cited

U.S. PATENT DOCUMENTS

| 3,891,573 | 6/1975 | Stavy et al. ...................... 252/408 R |
| 3,907,645 | 9/1975 | Richmond ...................... 195/103.5 R |
| 3,925,164 | 12/1975 | Beaucamp et al. ............ 195/103.5 R |
| 3,983,005 | 9/1976 | Goodhue et al. .............. 195/103.5 R |
| 3,985,621 | 10/1976 | Muruyama et al. ........... 195/103.5 R |

*Primary Examiner*—Thomas G. Wiseman
*Attorney, Agent, or Firm*—Sprung, Felfe, Horn, Lynch & Kramer

[57] ABSTRACT

Cholesterol is determined utilizing cholesterol oxidase, and optionally cholesterol esterase to cleave bound cholesterol, in the presence of peroxidase, p-aminophenazone, a surface-active agent and phenol, the improvement comprising employing an alkanol of up to 4 carbon atoms in the test composition or sample to substantially overcome test error and deviations due to turbidity formation.

7 Claims, No Drawings

PROCESS AND REAGENT FOR DETERMINING CHOLESTEROL

This is a continuation application of Ser. No. 695,332, filed June 14, 1976, now abandoned.

The present invention relates to a process for the enzymatic determination of cholesterol and to a reagent for carrying out this process.

The enzymatic determination of cholesterol with the help of cholesterol oxidase is known. The cholesterol is hereby oxidized with oxygen in the presence of cholesterol oxidase to give cholestenone and hydrogen peroxide. The reaction products can then be determined according to various methods.

A known method for the determination of hydrogen peroxide consists of the oxidative coupling thereof with p-amino-phenazone and phenol in the presence of peroxidase (see Ann. Clin. Biochem., 6, 24/1969). This reaction results in the formation of a chromogen with an absorption maximum at 500 nm which can easily be determined quantitatively with a photometer.

It is also known to apply this method for the determination of hydrogen peroxide in connection with the determination of cholesterol with cholesterol oxidase (see Clin. Chem., 20 470-476/1974). This method enables cholesterol to be determined in a simple manner. However, we have found that, in many cases, considerable deviations occur due to the formation of turbidity. It has admittedly proved to be possible, in many cases, to overcome the errors due to this turbidity, which usually cannot be seen with the naked eye, by measuring against a sample blank. However, in the case of a number of serum samples, turbidities arise, the effects of which cannot even be eliminated by means of a sample blank so that, in such cases, the process is completely useless. The reason for this is due to the different turbidities in the sample and sample blank, with the result that cholesterol values are obtained which are always too high.

In British Patent Specification No. 1,435,400, there is described and claimed a process for the activation of cholesterol oxidase, wherein at least one surface-active compound with lipophilic and hydrophilic properties is added to the cholesterol oxidase before use. The surface-active compound in questionn is preferably non-ionic and preferably contains at least one hydroxyl group. Furthermore, the surface-active compound is preferably used in an amount of from 0.005 to 0.1 wt.%, referred to the aqueous enzyme solution. The preferred non-ionic, surface-active compounds include the polyoxyethylene derivatives of alkyl, aryl and aralkyl alcohols.

The present invention substantially overcomes the disadvantages due to turbidity which occur in the above-described known process and provides an improvement of the invention of the above-mentioned British Patent Specification No. 1,435,400.

The present invention provides a process for the determination of cholesterol with cholesterol oxidase and optionally also cholesterol esterase in the presence of peroxidase, p-amino-phenazone, a surface-active agent and phenol, wherein at least one alkanol containing up to 4 carbon atoms is added to the test sample.

The preferred alkanol used according to the process of the present invention is methanol but ethanol, n-propanol, isopropanol and the butanols can also be used.

The amount of alkanol added can be varied, depending upon the particular conditions to be taken into account. Dependable results are always obtained with an addition of from 2 to 10 volume % alkanol, referred to the total volume of test batch. Particularly preferred is the addition of 5 to 9 volume % methanol or of 3 to 8 volume % of the higher alcohols.

As a rule, the process according to the present invention permits the complete omission of a sample blank in the cholesterol determination. In those cases in which hitherto the turbidities have been so strong that the determination could not be carried out at all give, by means of the process according to the present invention, dependable results when a sample blank is also included.

The process according to the present invention can be carried out not only for the determination of free cholesterol but also of bound (esterified) cholesterol. The determination of total (free and bound) cholesterol, which, in practice, is much more important, can be carried out in known manner by additionally adding cholesterol esterase or some other appropriate agent for the saponification of esterified cholesterol.

The present invention also provides a reagent for the carrying out of the determination of cholesterol. Such a reagent comprises cholesterol oxidase and optionally cholesterol esterase, as well as peroxidase, p-amino-phenazone, phenol, buffer and a surface-active agent, together with at least one alkanol containing up to 4 carbon atoms.

The surface-active agent used is preferably one of those disclosed in the above-mentioned British Patent Sepcification No. 1,435,400.

An especially preferred reagent according to the present invention comprises:
0.05 to 5 U cholesterol oxidase/5 ml reagent volume
0.2 to 2 U cholesterol esterase/5 ml reagent volume
0.03 to 3 U peroxidase/5 ml reagent volume
0.5 to 3 mM p-amiono-phenazone
2 to 15 mM phenol
0.05 to 1 weight % surface-active agent
0.2 to 1.0 M phosphate buffer (pH 7 to 8)
2 to 10 volume % methanol.

2 to 5 ml. of the above reagent suffice for one determination, including a sample blank. For larger batches, corresponding multiples thereof are employed.

For carrying out the process, the reagent according to the present invention, with the exception of the cholesterol oxidase, is mixed with a serum sample to be investigated so that there is obtained a total volume of from 2 to 3 ml. and then the extinction is determined in a photometer at an appropriate wavelength, for example at 546 nm. Thereafter, the cholesterol oxidase is added thereto and, after a definite period of time, the extinction difference is determined, which is a measure of the amount of cholesterol present in the serum sample.

The following examples illustrate the invention:

EXAMPLE 1

To 5 ml. 0.5M potassium phosphate buffer (pH 7.5), which contains 0.2% by weight hydroxypolyethoxydodecane (surface-active agent), 7.5% by volume methanol, 10 mM phenol and 1 mM 4-amino-phenazone, are added 0.05 ml. of a lipaemic serum, as well as 0.02 ml. (1 U) cholesterol esterase solution and 0.02 ml. (2 U) peroxidase. The sample is now divided up into two equal volumes and to one half (2.5 ml.) is added 0.02 ml. cholesterol oxidase solution (0.2 U).

After incubation of both solutions (with and without cholesterol oxidase) at 37° C. for 15 minutes or at ambient temperature for 30 minutes, the solution containing the cholesterol oxidase is measured against the solution without cholesterol oxidase at 546 nm. The extinction difference thereby measured is a measure of the cholesterol concentration in the serum, which is calculated with reference to a cholesterol standard measured at the same time.

The cholesterol content for a typical sample gives 367 mg. cholesterol/100 ml. and a comparative determination by the catalase method (see Z. X. Klin. Chem. Klin. Biochem., 12, 403–407/1974) gives 369 mg. cholesterol/100 ml.

When the determination is carried out in the absence of methanol, then a turbidity occurs which makes impossible the measurement of the extinction at 546 nm and thus the determination of the cholesterol concentration is also impossible.

EXAMPLE 2

To 2 ml. 0.5 M potassium phosphate buffer (pH 7.5), which contains 0.2% by weight hydroxypolyethoxydodecane, 7.5% by volume methanol, 10 mM phenol and 1 mM 4-amino-phenazone, are added 0.02 mL. serum, as well as 0.02 ml. (1 U) cholesterol esterase, 0.02 ml. (2 U) peroxidase and 0.02 ml. (0.2 U) cholesterol oxidase solution. After incubation at 37° C. for 15 minutes or at ambient temperature for 30 minutes, this solution is measured at 546 nm against a reagent blank (i.e., instead of the sample, water is added to the determination batch). The cholesterol content of the serum-containing sample is determined, with reference to a cholesterol standard measured at the same time.

The cholesterol content for a typical sample gives 253 mg. cholesterol/100 ml. and a comparative determination by the catalase method gives 251 mg. cholesterol/100 ml.

When this determination is carried out in the absence of methanol, then 15% higher cholesterol values are found.

It will be understood that the specification and examples are illustrative but not limitative of the present invention and that other embodiments within the spirit and scope of the invention will suggest themselves to those skilled in the art.

What is claimed is:

1. Process for the determination of total cholesterol, which process comprises saponifying any bound cholesterol in the sample by reacting same with cholesterol esterase and determining free cholesterol utilizing cholesterol oxidase in the presence of peroxidase, p-aminophenazone, a surface-active agent and phenol, wherein at least one alkanol containing up to 4 carbon atoms is added to the test sample, in an amount to solubilize turbidity-causing complexes and then determining the formation of the resulting chromogen as a measure of the initial total cholesterol content.

2. Process for the determination of cholesterol as claimed in claim 1 wherein 2 to 10 volume % of alkanol are added, referred to the total test sample.

3. Process for the determination of cholesterol as claimed in claim 2 wherein 5 to 9 volume % methanol are added, referred to the total test sample.

4. Process for the determination of cholesterol as claimed in claim 2 wherein 3 to 8 volume % of an alkanol containing 2 to 4 carbon atoms is added, referred to the total test sample.

5. Process for the determination of cholesterol as claimed in claim 1 utilizing 0.05 to 5 U cholesterol oxidase, 0.2 to 2 U cholesterol esterase, 0.03 to 3 U peroxidase each per 5 ml reagent volume, 0.5 to 3 mM p-amino-phenazone, 2 to 15 mM phenol, 0.05 to 1% by weight surface-active agent, 0.2 to 1.0 M phosphate buffer (pH 7 to 8) and 2 to 10 volume % methanol.

6. Reagent for the determination of cholesterol comprising:
cholesterol oxidase,
peroxidase,
p-amino-phenazone
phenol,
buffer,
surface-active agent
at least one alkanol containing up to 4 carbon atoms in an amount sufficient to solubilize turbidity causing complexed in a serum sample, and
cholesterol esterase.

7. Reagent for the determination of cholesterol as claimed in claim 1 comprising 0.05 to 5 U cholesterol oxidase, 0.2 to 2 U cholesterol esterase, 0.03 to 3 U peroxidase each per 5 ml reagent volume, 0.5 to 3 mM p-amino-phenazone, 2 to 15 mM phenol, 0.05 to 1% by weight surface-active agent, 0.2 to 1.0 M phosphate buffer (pH 7 to 8) and 2 to 10 volume % methanol.

* * * * *